United States Patent
Ollerdessen et al.

(10) Patent No.: US 8,515,512 B2
(45) Date of Patent: *Aug. 20, 2013

(54) OPAQUE, ELECTRICALLY NONCONDUCTIVE REGION ON A MEDICAL SENSOR

(75) Inventors: Albert L. Ollerdessen, Danville, CA (US); Bradford B. Chew, San Ramon, CA (US); Phillip S. Palmer, San Leandro, CA (US)

(73) Assignee: Covidien LP, Mansfield, MA (US)

( * ) Notice: Subject to any disclaimer, the term of this patent is extended or adjusted under 35 U.S.C. 154(b) by 333 days.

This patent is subject to a terminal disclaimer.

(21) Appl. No.: 12/952,815

(22) Filed: Nov. 23, 2010

(65) Prior Publication Data
US 2011/0066016 A1 Mar. 17, 2011

Related U.S. Application Data

(63) Continuation of application No. 11/527,762, filed on Sep. 26, 2006, now Pat. No. 7,869,849.

(51) Int. Cl.
*A61B 5/1455* (2006.01)
(52) U.S. Cl.
USPC .......................................... 600/323; 600/344
(58) Field of Classification Search
USPC .................................. 600/323, 344
See application file for complete search history.

(56) References Cited

U.S. PATENT DOCUMENTS

| | | |
|---|---|---|
| 4,685,464 A | 8/1987 | Goldberger et al. |
| 4,830,014 A | 5/1989 | Goodman et al. |
| 5,099,842 A | 3/1992 | Mannheimer et al. |
| 5,237,994 A | 8/1993 | Goldberger |
| 5,246,003 A | 9/1993 | DeLonzor |
| 5,263,244 A | 11/1993 | Centa et al. |
| 5,368,025 A | 11/1994 | Young et al. |
| 5,390,670 A | 2/1995 | Centa et al. |
| 5,425,360 A | 6/1995 | Nelson |
| 5,438,986 A | 8/1995 | Disch et al. |
| 5,469,845 A | 11/1995 | DeLonzor et al. |
| 5,638,593 A | 6/1997 | Gerhardt et al. |
| 5,671,529 A | 9/1997 | Nelson |
| 5,676,139 A | 10/1997 | Goldberger et al. |
| 5,752,914 A | 5/1998 | DeLonzor et al. |
| 5,795,292 A | 8/1998 | Lewis et al. |
| 5,807,248 A | 9/1998 | Mills |
| 5,817,008 A | 10/1998 | Rafert et al. |
| 5,839,439 A | 11/1998 | Nierlich et al. |
| 5,891,021 A | 4/1999 | Dillon et al. |
| 5,891,026 A | 4/1999 | Wang et al. |
| 5,910,108 A | 6/1999 | Solenberger |
| 5,913,819 A | 6/1999 | Taylor et al. |
| 5,924,982 A | 7/1999 | Chin |

(Continued)

FOREIGN PATENT DOCUMENTS

| | | |
|---|---|---|
| EP | 1491135 | 12/2004 |
| EP | 1830695 | 9/2007 |

(Continued)

*Primary Examiner* — Eric Winakur
(74) *Attorney, Agent, or Firm* — Fletcher Yoder, P.C.

(57) ABSTRACT

A medical sensor may be adapted to prevent unwanted light and electrical interference from corrupting physiological measurements. Sensors are provided with features that reduce the amount of outside light or shunted light that impinge the detecting elements of the sensor. The sensor is adapted to reduce crosstalk between electrical signals, increasing the accuracy of measurements. The sensor is also adapted to reduce the effect of outside light or shunted light on pulse oximetry measurements.

20 Claims, 5 Drawing Sheets

(56) References Cited

U.S. PATENT DOCUMENTS

| | | |
|---|---|---|
| 5,940,182 A | 8/1999 | Lepper, Jr. et al. |
| 5,960,610 A | 10/1999 | Levinson et al. |
| 6,112,107 A | 8/2000 | Hannula |
| 6,149,481 A | 11/2000 | Wang et al. |
| 6,278,522 B1 | 8/2001 | Lepper, Jr. et al. |
| 6,745,061 B1 | 6/2004 | Hicks et al. |
| 6,760,607 B2 | 7/2004 | Al-All |
| 6,763,255 B2 | 7/2004 | DeLonzor et al. |
| 6,830,711 B2 | 12/2004 | Mills et al. |
| 6,850,788 B2 | 2/2005 | Al-Ali |
| 6,943,348 B1 | 9/2005 | Coffin, IV |
| 7,369,886 B2 | 5/2008 | DeLonzor et al. |
| 7,373,188 B2 | 5/2008 | DeLonzor et al. |
| 7,373,189 B2 | 5/2008 | DeLonzor et al. |
| 7,373,190 B2 | 5/2008 | DeLonzor et al. |
| 7,373,191 B2 | 5/2008 | DeLonzor et al. |
| 7,389,130 B2 | 6/2008 | DeLonzor et al. |
| 7,561,905 B2 | 7/2009 | DeLonzor et al. |
| 2002/0103423 A1 | 8/2002 | Chin et al. |
| 2003/0018243 A1 | 1/2003 | Gerhardt et al. |
| 2003/0132495 A1 | 7/2003 | Mills et al. |
| 2006/0229508 A1 | 10/2006 | Kermani et al. |
| 2007/0032712 A1 | 2/2007 | Raridan et al. |
| 2007/0032713 A1 | 2/2007 | Eghbal et al. |
| 2007/0032716 A1 | 2/2007 | Raridan et al. |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076996 A1 | 3/2008 | Hoarau |
| 2008/0081967 A1 | 4/2008 | Andersohn et al. |

FOREIGN PATENT DOCUMENTS

| | | |
|---|---|---|
| EP | 1945099 | 7/2008 |
| JP | 200237170 | 9/2000 |
| WO | WO0059374 | 10/2000 |
| WO | WO2006006158 | 1/2006 |

OPAQUE, ELECTRICALLY NONCONDUCTIVE REGION ON A MEDICAL SENSOR

CROSS REFERENCE TO RELATED APPLICATIONS

This application is a continuation of prior U.S. application Ser. No. 11/527,762, filed Sep. 26, 2006, the specification of which is incorporated by reference in its entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to certain aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry measures various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that emits light into a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount related to the amount of a particular constituent present in the blood. The amount of light absorbed and/or scattered may then be used to estimate the amount of the blood constituent in the tissue using various algorithms.

The pulse oximetry measurement depends in part on the assumption that the contribution of light that has not passed through a patient's tissue is negligible. However, outside light may leak into a sensor, causing detection of light that is not related to the amount of blood constituent present in the blood. Additionally, shunted light or light from a sensor's emitter, may be reflected around the exterior of the tissue and may be sensed by the detector without traveling first through the tissue. These light sources may cause measurement variations that result in erroneous blood constituent readings.

Some outside light infiltration into the sensor may be avoided by fitting the sensor snugly against the patient's tissue. However, such a conforming fit may be difficult to achieve over a broad range of patient physiologies without adjustment or excessive attention on the part of medical personnel. Additionally, an overly tight fit may cause local exsanguination of the tissue around the sensor. Exsanguinated tissue, which is devoid of blood, may shunt the sensor light through the tissue, which may also result in increased measurement errors.

External light and shunted light may also be prevented from reaching the sensor by certain coatings applied to the pulse oximetry device. For example, some sensors incorporate reflective coating on the tissue contacting surface to reflect shunted light away from the detector. However, these reflective materials are metal-based, and thus conductive, which may result in capacitive coupling between the emitter and detector. In particular, conductive reflective materials may provide electrical paths between the pulse oximeter's light emitter and the detector. These electrical paths may cause corruption of the detector's measurement signal, resulting in an incorrect reading of more or less absorption of light than is actually transmitted through the patient's tissue. Therefore, noise added to the signal by crosstalk can lead to erroneous physiological measurements.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; an emitter disposed on the sensor body, wherein the emitter is adapted to transmit light into tissue; a detector disposed on the sensor body, wherein the detector is adapted to detect the light; and at least one opaque region disposed on a tissue-contacting surface of the sensor body, the opaque region including a substantially electrically nonconductive material.

There is also provided a pulse oximetry system that includes a pulse oximetry monitor and a pulse oximetry sensor adapted to be operatively coupled to the monitor. The sensor includes: a sensor body; and at least one opaque region, the opaque region disposed on a tissue-contacting surface of the sensor body, including a substantially electrically nonconductive material.

There is also provided a method that includes: emitting light into tissue with an emitter; detecting the emitted light with a detector; absorbing light that has not been transmitted from the emitter through the tissue with at least one opaque region, wherein the at least one opaque region includes a substantially electrically nonconductive material; and measuring a physiological characteristic based on the detected light.

There is also provided a method of manufacturing a sensor that includes: providing a sensor body on which at least one sensing element is disposed; and providing at least one opaque region disposed on a tissue-contacting surface of the sensor body, the opaque region includes a nonconductive material.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
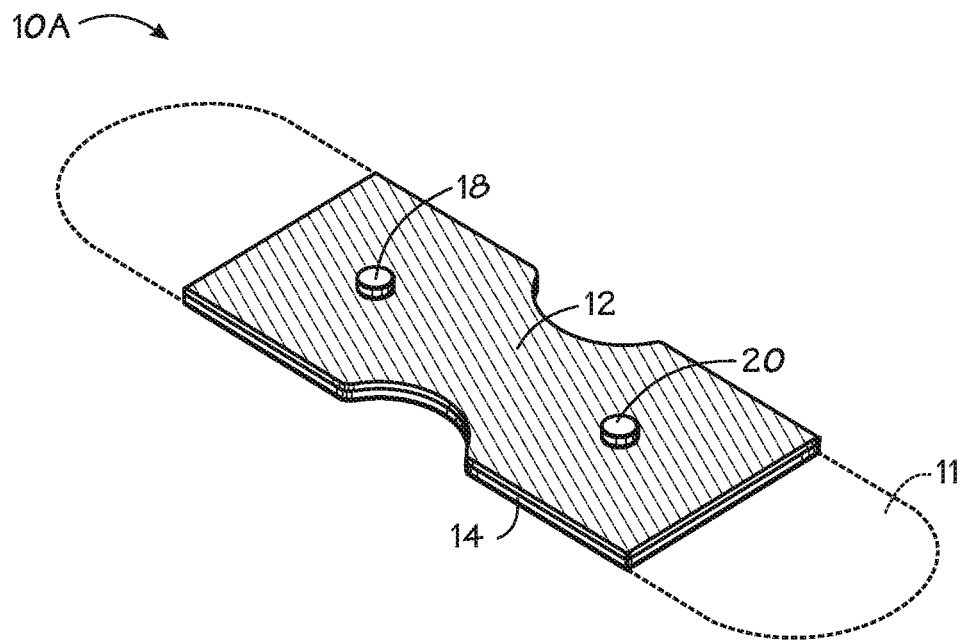
FIG. 1 illustrates a perspective view of an embodiment of an exemplary bandage-style sensor with an opaque, electrically nonconductive region in accordance with the present invention.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to eliminate or reduce the possible influence of light sources which may cause errors in pulse oximetry measurements. In accordance with the present techniques, pulse oximetry sensors are provided that reduce the amount of outside light that impinges the detecting elements of a sensor. Such sensors also reduce the amount of "shunted" light, i.e., light originating from light emitting elements of the sensor that impinges the detecting elements of a sensor without first passing through tissue. Sensors according to the present techniques incorporate features, such as a region of opaque material, on or near the tissue-contacting surface of the sensor, to prevent the undesired light from reaching the detecting elements of the sensor. Such regions may absorb, refract, or diffract the light from these undesired light sources before such light can impinge the detecting elements of the sensor.

The present sensors minimize the detection of unwanted external or shunted light to the sensor by application of an opaque, electrically nonconductive material to the body of the sensor. A substantially electrically nonconductive material may reduce electrical paths, interference and crosstalk between electrical signals. An opaque material is one that is substantially impenetrable by light and is not translucent. The opaque characteristics prevent external light from penetrating the region covered by opaque material while also absorbing shunted light.

Pulse oximetry sensors are typically placed on a patient in a location that is normally perfused with arterial blood to facilitate measurement of the desired blood characteristics, such as arterial oxygen saturation measurement ($SpO_2$). The most common sensor sites include a patient's fingertips, toes, earlobes or forehead. Regardless of the placement of a sensor used for pulse oximetry, the reliability of the measurement depends upon accurate detection of transmitted light that has passed through the perfused tissue which has not been supplemented by undesired light sources, such as external light or shunted light. Such supplementation or modulation of the light detected by the sensor can cause errors in the resulting pulse oximetry measurements.

In many cases, light from undesired light sources propagates along an optical path that is distinguishable from the optical path of the emitted light or signal light that is related to a blood constituent. Two common pulse oximetry sensors are the transmission-type sensor and the reflectance-type sensor. In a transmission-type sensor, the sensor's emitter and detector are positioned on opposing sides of the tissue when the sensor is applied to a patient. The optical path of the signal light, which is light originating from the emitter that properly passes through perfused tissue, is substantially in-line with an imaginary axis connecting the emitter and the detector. For reflectance-type sensors, the sensor's emitter and detector generally lie on the same side of the patient's tissue when applied. In reflectance-type sensors, the optical path of the emitted signal light is somewhat more complicated, as the light first enters the perfused tissue and then is scattered back to the detector. In both transmission-type and reflectance-type sensors, shunted light and ambient light generally propagate at angles substantially off-axis from the optical path of the signal light.

The exemplary sensors provided herein include opaque nonconductive regions that act to prevent shunted or external light from impinging on the light detecting elements of a sensor. In certain embodiments, those regions may be disposed on the sensor as layers, patterns, designs or a combination thereof. Specifically, FIG. 1 illustrates a perspective view of an embodiment of an exemplary bandage-style sensor 10A with an opaque, electrically nonconductive region 12 disposed on the sensor body 14. As one with skill in the art understands, the opaque, electrically nonconductive region 12 may be actually touching a patient's tissue, or may be almost touching the patient's tissue, depending on the closeness of the sensor's fit. As depicted, the region 12 is disposed on the entire tissue contacting surface of the sensor body 14, surrounding the emitter 20 and the detector 18. The sensor 10A may be applied to a patient's tissue with adhesive bandages 11. In certain embodiments, the opaque, electrically nonconductive region 12 may also include an adhesive layer configured to couple the region 12 to the patient.

Generally, it is envisioned that the opaque, electrically nonconductive region 12 will cover at least 75% of the tissue contacting surface of sensor body 14. In other embodiments, the opaque, electrically nonconductive region 12 may cover at least 25-65% of the surface area of the sensor body 14. The opaque, electrically nonconductive region 12 may be of variable size and configuration in relation to its placement on the sensor body 14 so as to optimize shielding from unwanted shunted and ambient light. In one embodiment, where the opaque, electrically nonconductive region 12 covers a portion of the tissue contacting surface, it is placed between emitter 20 and detector 18.

Figure 2:
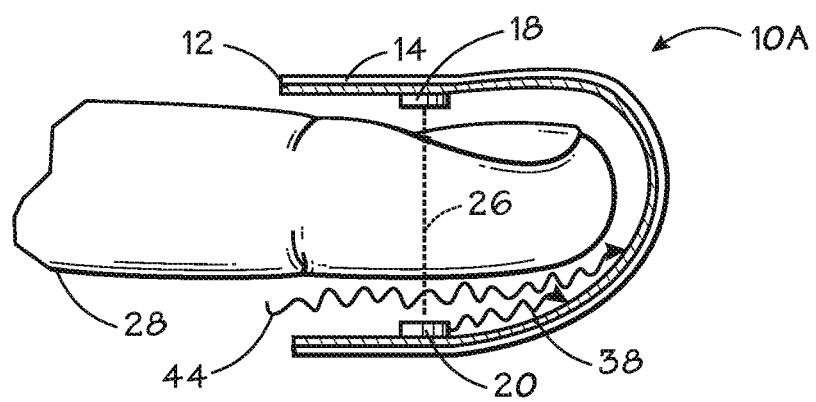
FIG. 2 illustrates a cross-sectional view of an embodiment of an exemplary bandage-style sensor with an opaque, electrically nonconductive region applied to the patient's digit.

Turning to FIG. 2, a cross-sectional view of the sensor 10A is depicted, in which a sensor body 14 including substantially opaque, electrically nonconductive region 12 is applied to a patient's digit 28. As depicted, the region 12 is disposed on a tissue-contacting surface of the sensor body 14. The optical path of signal light originating from the emitter 20 and through a patient's tissue is substantially in-line with an imaginary axis 26 connecting the emitter 20 and the detector 18. The detector 18 detects light and transmits the light measurement in the form of an electrical signal. A small percentage of the light emitted by the emitter 20 may not enter the perfused digit 28. Instead, this light may be shunted around the space between the digit 28 and the sensor body 14. The shunted light, depicted by wavy arrow 38, impinges the opaque, electrically nonconductive region 12, which absorbs the light, thus preventing it from reflecting around the gap between the sensor body 14 and the digit 28 and impinging on the detector 18. External light, depicted by wavy arrow 44, is similarly absorbed by the opaque, electrically nonconductive region 12. It should be understood that the gap between the sensor body 14 and the digit 28 may be very small for a sensor body 14 that conforms closely to the digit 28. Further, the gap may be discontinuous when interrupted by points where the sensor body 14 is touching the digit 28. The opaque region 12 reduces the overall reflectivity of the sensor body 14 on the tissue-contacting surface, which may reduce the amount of shunted light that reaches the detector 18. In addition, the substantially electrically nonconductive characteristic of region 12 reduces electrical interference and crosstalk between signals from the emitter 20 and detector 18, which may result in a reduction of measurement errors.

In certain embodiments, the opaque, electrically nonconductive region 12 as provided herein may include a material that may absorb at least about 90% to at least 95% of one or more wavelengths of visible light and near-infrared light. An opaque material may also absorb at least 50% of one or more wavelengths of light from the emitter, or may absorb a range of 50% to 95% of one or more wavelengths of light from the emitter. Examples of materials that may be used for the opaque, electrically nonconductive region 12 include nonconductive polymers, pigments, epoxy, fabrics (e.g. polyester-based materials) and silicone-based materials. The region 12 may be black or substantially dark in color. However, a thick light-colored region may also be sufficiently opaque. An opaque, electrically nonconductive region 12 may be applied to the sensor body 14 by painting, printing, or impregnating a film on the sensor body 14, or by adhesively applying the region 12 as a layer to the sensor body 14. The opaque, electrically nonconductive region 12 can be of variable thickness and may be one or more layers, depending upon the materials or application technique selected. The opaque, electrically nonconductive region 12 may be generally flexible, so as to allow the sensor 10 to conform to the patient's tissue. In certain embodiments, the opaque, electrically nonconductive region 12 is approximately 0.5 to 2.5 mils thick.

Figure 3:
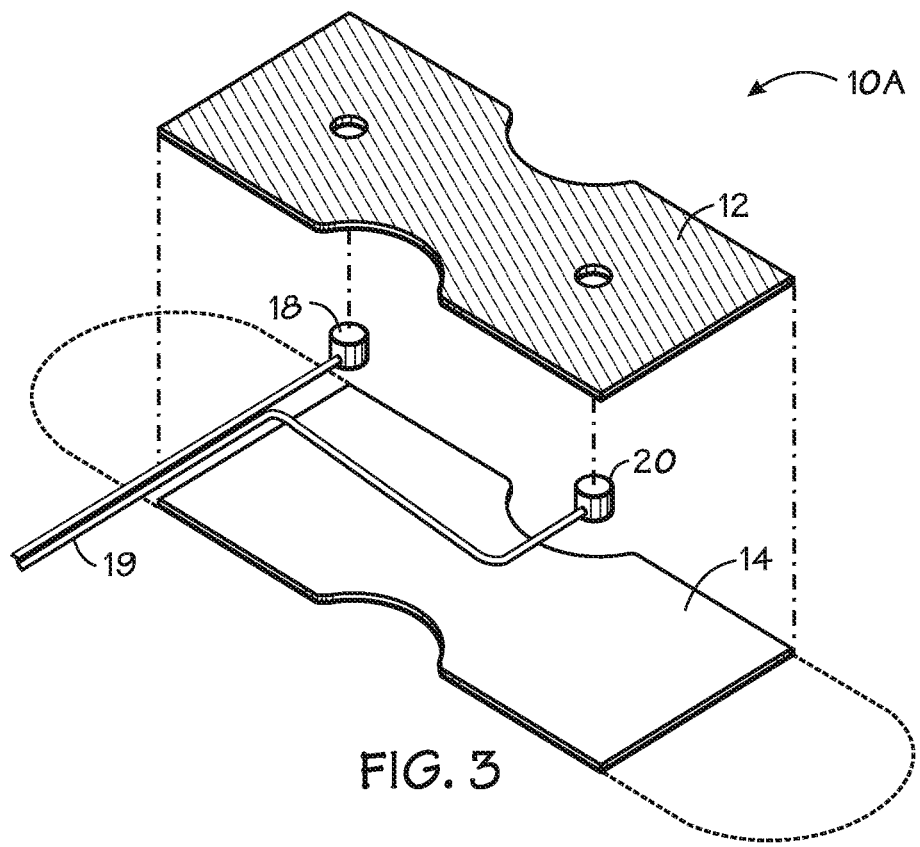
FIG. 3 illustrates an exploded view of the sensor of FIG. 1.

For example, FIG. 3 illustrates an exploded view of an embodiment of the bandage-style sensor 10A with an opaque, electrically nonconductive region 12 disposed on the sensor body 14. In certain embodiments, the emitter 20 and the detector 18 may be placed between the sensor body 14 and the opaque, electrically nonconductive region 12, protruding through holes in the opaque, electrically nonconductive region 12. The emitter 20 and detector 18 have leads 19 which connect the sensor 10A to the pulse oximetry system. As depicted, leads 19 are positioned near the center of sensor body 14, connecting the emitter 20 and detector 18 to a monitoring device. The opaque, electrically nonconductive region 12 is disposed to shield the leads 19, the emitter 20 and the detector 18, reducing crosstalk between signals.

Figure 4:
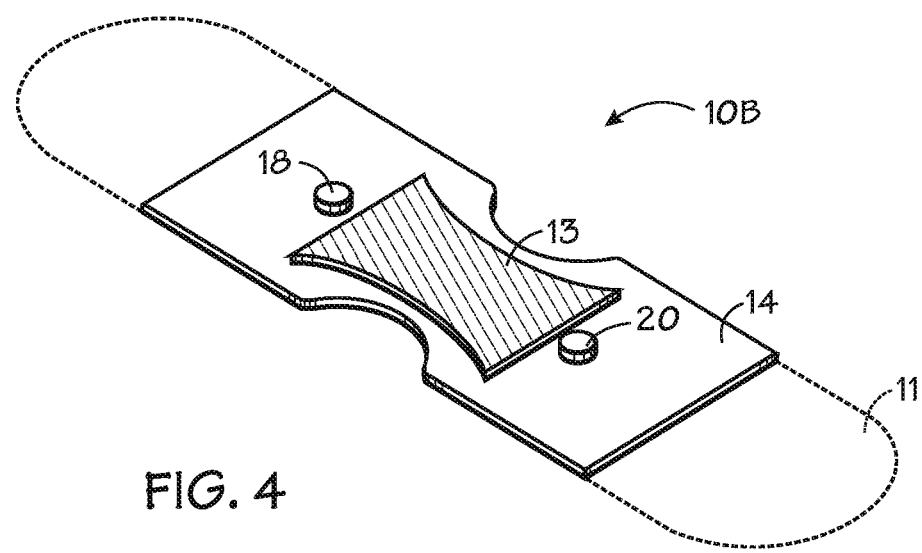
FIG. 4 illustrates a perspective view of an embodiment of an exemplary bandage-style sensor with an opaque, electrically nonconductive region disposed between the emitter and detector, in accordance with the present invention.
Figure 5:
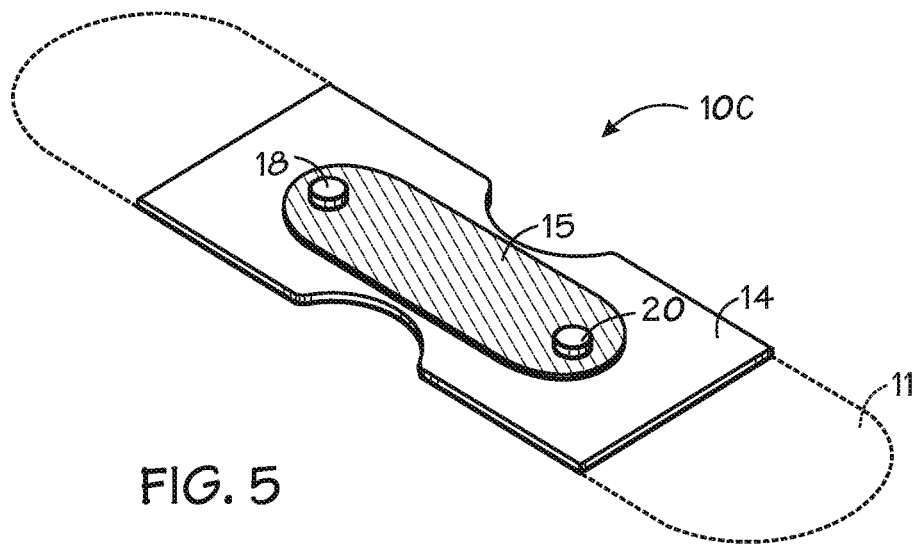
FIG. 5 illustrates a perspective view of an embodiment of an exemplary bandage-style sensor with an opaque, electrically nonconductive region in accordance with the present invention.

In certain embodiments, it may be advantageous to place opaque regions of differing patterns or designs on the sensor body. For example, FIG. 4 and FIG. 5 illustrate perspective views of bandage-style sensors with opaque nonconductive regions disposed on the sensor body. FIG. 4 illustrates a sensor 10B where the opaque, electrically nonconductive region 13 is disposed on the sensor body 14 between the emitter 20 and the detector 18. In an alternative embodiment, FIG. 5 illustrates a sensor 10C where the opaque, electrically nonconductive region 15, disposed on the sensor body 14, surrounds the emitter 20 and the detector 18. FIGS. 4 and 5 both depict adhesive bandages 11 for affixing the sensor to the patient's digit.

Figure 6:
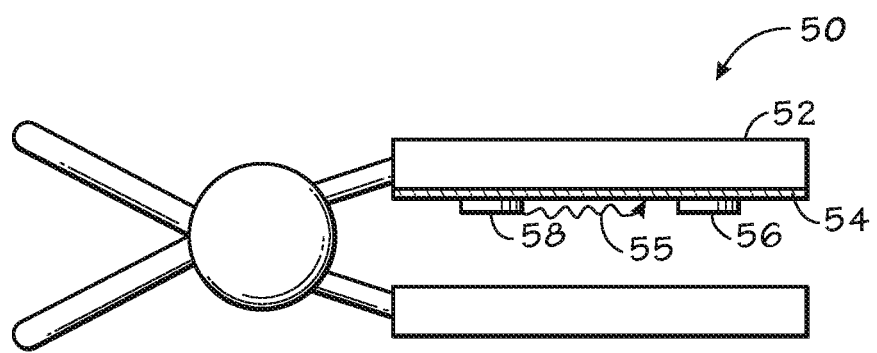
FIG. 6 illustrates a side view of an embodiment of an exemplary clip-style reflectance sensor with an opaque, electrically nonconductive region in accordance with the present invention.

FIG. 6 illustrates a side view of an embodiment of an exemplary clip-style reflectance sensor 50 with the opaque, electrically nonconductive region 54 disposed on the sensor body 52. In certain embodiments, the opaque, electrically nonconductive region 54 may be disposed on the entire tissue-contacting surface of the portion of the sensor body 52 where an emitter 58 and a detector 56 are disposed. As the emitted light, depicted by wavy arrow 55, strikes the opaque region 54, it is absorbed, preventing the unwanted light from impinging the detector 56. As stated above, it is desirable to avoid detection of the emitted light 55 as it has not traveled through the patient's tissue. The opaque, electrically nonconductive region 54 is disposed to shield the wire leads (not shown) to the emitter 58 and detector 56, reducing crosstalk between signals that may be transmitted to a downstream monitoring device, discussed below.

Figure 7:
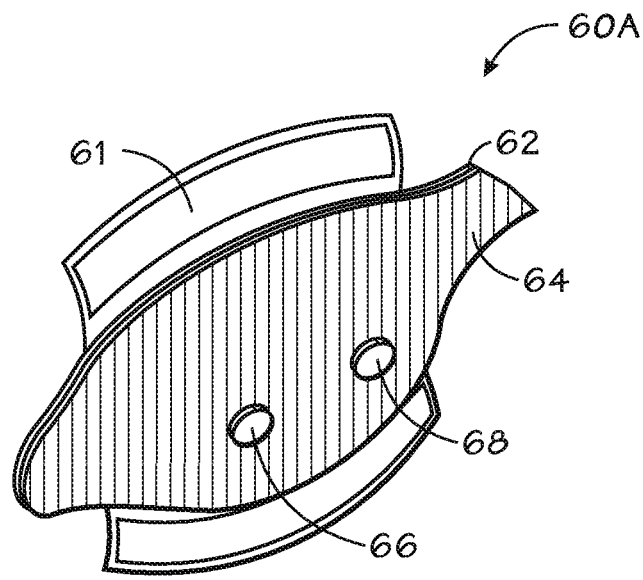
FIG. 7 illustrates a perspective view of an embodiment of an exemplary bandage-style reflectance sensor with an opaque, electrically nonconductive region in accordance with the present invention.
Figure 8:
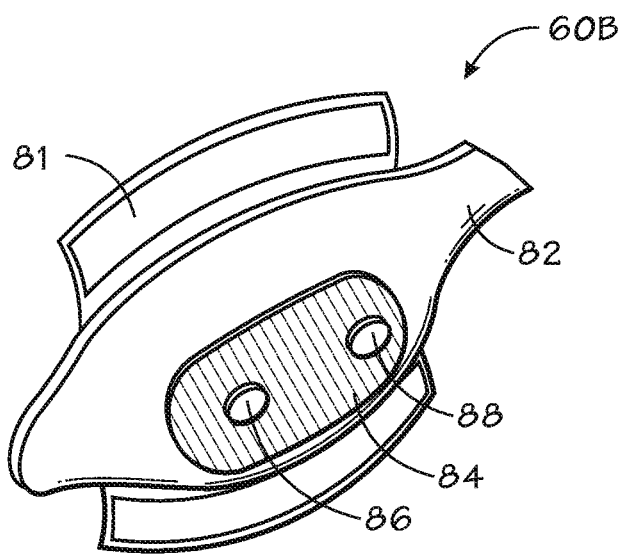
FIG. 8 illustrates a perspective view of an embodiment of an exemplary bandage-style reflectance sensor with an opaque, electrically nonconductive region in accordance with the present invention.

In another embodiment, FIG. 7 illustrates a perspective view of an exemplary bandage-style forehead sensor 60A with an opaque, electrically nonconductive region 64 disposed on a sensor body 62. The opaque, electrically nonconductive region 64 may be disposed on the entire tissue-contacting surface of the sensor body 62, surrounding emitter 68 and the detector 66. Alternatively, FIG. 8 illustrates an embodiment of an exemplary bandage-style reflectance sensor 60B with an opaque, electrically nonconductive region 84 disposed on a portion of the sensor body 82. As shown, the opaque, electrically nonconductive region 84 surrounds an emitter 88 and a detector 86. FIGS. 7 and 8 depict adhesive bandages 61 and 81, respectively, for affixing the sensor to the patient's tissue.

Figure 9:
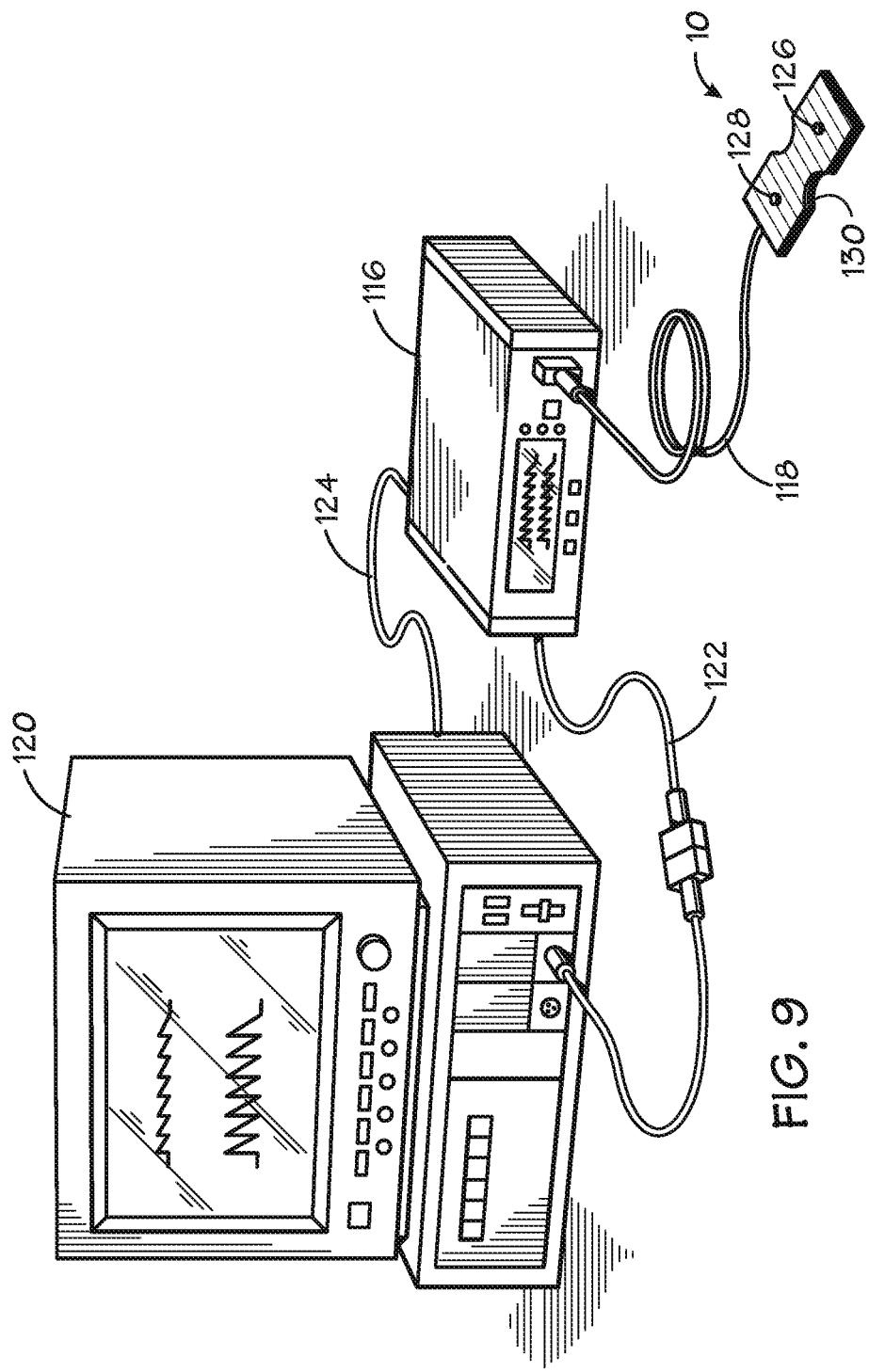
FIG. 9 illustrates a pulse oximetry system coupled to a multi-parameter patient monitor and a sensor according to embodiments of the present invention.

A sensor as provided herein, illustrated generically as a sensor 10, may be used in conjunction with a pulse oximetry monitor 116, as illustrated in FIG. 9. It should be appreciated that the cable 118 of the sensor 10 may be coupled to the monitor 116 or it may be coupled to a transmission device (not shown) to facilitate wireless transmission between the sensor 10 and the monitor 116. The monitor 116 may be any suitable pulse oximeter, such as those available from Nellcor Inc. Furthermore, to upgrade conventional pulse oximetry provided by the monitor 116 to provide additional functions, the monitor 116 may be coupled to a multi-parameter patient monitor 120 via a cable 122 connected to the sensor input port or via a cable 124 connected to a digital communication port.

The sensor 10 includes an emitter 128 and a detector 126 that may be of any suitable type. For example, the emitter 128 may be one or more light emitting diodes adapted to transmit one or more wavelengths of light in the red to infrared range, and the detector 126 may be a photodetector selected to receive light in the range or ranges emitted from the emitter 128. For pulse oximetry applications using either transmission or reflectance type sensors, the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 128 and the detector 126 may be disposed on a sensor body 130, which may be made of any suitable material, such as plastic, rubber, silicone, foam, woven material, or paper. Alternatively, the emitter 128 and the detector 126 may be remotely located and optically coupled to the sensor 10 using optical fibers. In the depicted embodiments, the sensor 10 is coupled to a cable 118 that is responsible for transmitting electrical and/or optical signals to and from the emitter 128 and detector 126 of the sensor 10. The cable 118 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 128 and detector 126 that are typically placed on opposing sides of the sensor site. If the sensor site is a fingertip, for example, the sensor 10 is positioned over the patient's fingertip such that the emitter 128 and detector 126 lie on either side of the patient's nail bed. In other words, the sensor 10 is positioned so that the emitter 128 is located on the patient's fingernail and the detector 126 is located 180° opposite the emitter 128 on the patient's finger pad. During operation, the emitter 128 shines one or more wavelengths of light through the patient's fingertip and the light received by the detector 126 is processed to determine various physiological characteristics of the patient. In each of the embodiments discussed herein, it should be understood that the locations of the emitter 128 and the detector 126 may be exchanged. For example, the detector 126 may be located at the top of the finger and the emitter 128 may be located underneath the finger. In either arrangement, the sensor 10 will perform in substantially the same manner.

Reflectance type sensors generally operate under the same general principles as transmittance type sensors. However, reflectance type sensors include an emitter 128 and detector 126 that are typically placed on the same side of the sensor site. For example, a reflectance type sensor may be placed on a patient's fingertip or forehead such that the emitter 128 and detector 126 lay side-by-side. Reflectance type sensors detect light photons that are scattered back to the detector 126.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A pulse oximetry system comprising:
   a pulse oximetry monitor; and
   a pulse oximetry sensor adapted to be operatively coupled to the monitor, the sensor comprising:
   a sensor body supporting respective electrical connectors connected to an emitter and a detector, wherein the emitter and the detector are disposed on a tissue-contacting surface of the sensor body; and
   at least one opaque member disposed on the sensor body and spanning only a portion of the sensor body between the emitter and the detector, the opaque member comprising a substantially electrically nonconductive material, and wherein the opaque member does not surround the emitter and detector.

2. The system, as set forth in claim 1, wherein the at least one opaque member comprises a polyester-based material.

3. The system, as set forth in claim 1, wherein the at least one opaque member comprises a silicone-based material.

4. The system, as set forth in claim 1, wherein the at least one opaque member is conformable to the tissue.

5. The system, as set forth in claim 1, wherein the emitter comprises at least one light emitting diode and the detector comprises at least one photodetector.

6. The system, as set forth in claim 1, wherein the at least one opaque member is substantially dark in color.

7. The system, as set forth in claim 1, wherein the at least one opaque member is substantially light in color.

8. The system, as set forth in claim 1, wherein the sensor comprises a bandage-type sensor.

9. The system, as set forth in claim 8, wherein the bandage-type sensor is configured for use on a digit.

10. The system, as set forth in claim 1, wherein the sensor comprises a transmission-type sensor.

11. The system, as set forth in claim 1, wherein the sensor comprises a reflectance-type sensor.

12. A sensor comprising:
    a sensor body supporting respective electrical connectors connected to an emitter and a detector, wherein the emitter and the detector are disposed on a tissue-contacting surface of the sensor body; and
    at least one opaque member disposed on the sensor body and covering at least a portion of the sensor body corresponding to an area of the sensor body supporting respective electrical leads coupled to the emitter and the detector, the opaque member comprising a substantially electrically nonconductive material, and wherein the opaque member does not surround the emitter and detector.

13. The sensor, as set forth in claim 12, wherein the sensor comprises at least one of a pulse oximetry sensor or a sensor for measuring a water fraction.

14. The sensor, as set forth in claim 12, wherein the at least one opaque member is disposed on at least 90% of the sensor body.

15. The sensor, as set forth in claim 12, wherein the sensor is configured for use on a digit.

16. The sensor, as set forth in claim 12, wherein the sensor comprises a transmission-type sensor.

17. The sensor, as set forth in claim 12, wherein the sensor comprises a reflectance-type sensor.

18. A pulse oximetry sensor comprising:
a conformable sensor body supporting respective electrical connectors connected to an emitter and a detector, wherein the emitter and the detector are disposed on a tissue-contacting surface of the sensor body; and
at least one opaque member disposed on the sensor body between the emitter and the detector such that the opaque member is disposed in an area corresponding to at least a portion of an imaginary axis connecting the emitter and the detector, the opaque member comprising a substantially electrically nonconductive material, and wherein the opaque member does not surround the emitter and detector.

19. The sensor, as set forth in claim 18, wherein the pulse oximetry sensor comprises a digit sensor.

20. The sensor, as set forth in claim 18, wherein the pulse oximetry sensor comprises a transmission-type sensor.

* * * * *